United States Patent [19]
Kesling

[11] Patent Number: 5,125,832
[45] Date of Patent: * Jun. 30, 1992

[54] BRACKET FOR PERMITTING TIPPING AND LIMITING UPRIGHTING

[75] Inventor: Peter C. Kesling, LaPorte, Ind.

[73] Assignee: TP Orthodontics, Inc., Westville, Ind.

[*] Notice: The portion of the term of this patent subsequent to Oct. 3, 2006 has been disclaimed.

[21] Appl. No.: 400,321

[22] Filed: Aug. 31, 1989

Related U.S. Application Data

[63] Continuation of Ser. No. 54,837, Jun. 4, 1987, Pat. No. 4,877,398, which is a continuation-in-part of Ser. No. 39,530, Apr. 16, 1987, abandoned, which is a continuation-in-part of Ser. No. 897,072, Jun. 26, 1986, abandoned.

[51] Int. Cl.⁵ .................................................. A61C 3/00
[52] U.S. Cl. .......................................... 433/8; 433/16
[58] Field of Search .............. 433/8, 9, 10, 11, 15, 433/16

[56] References Cited

U.S. PATENT DOCUMENTS

| | | | |
|---|---|---|---|
| 3,438,132 | 4/1969 | Rubin | 433/11 |
| 3,879,850 | 4/1975 | Wallshein | 433/11 |
| 3,959,880 | 6/1976 | Andrews | 433/11 |
| 4,180,912 | 1/1980 | Kesling | 433/8 |
| 4,353,692 | 10/1982 | Karrakussoglu | 433/16 |
| 4,487,581 | 12/1984 | Adler | 433/16 |
| 4,529,382 | 7/1985 | Creekmore | 433/9 |
| 4,531,911 | 7/1985 | Creekmore | 433/8 |
| 4,664,626 | 5/1987 | Kesling | 433/8 |

OTHER PUBLICATIONS

"Principles and Technique of Modified Edgewise Arch Mechanism", American Journal of Orthodontia and Oral Surgery, Jul. 1938, p. 639.
All Stage Bracket, Amjo, vol. 48, #5, May 1962, p. 22.

Primary Examiner—Gene Mancene
Assistant Examiner—Adriene B. Lepiane
Attorney, Agent, or Firm—Lloyd L. Zickert

[57] ABSTRACT

An orthodontic bracket having a horizontal archwire slot and wire-engaging surfaces for use in any treatment technique and coacting with an archwire and force generating means to produce tooth movement through crown tipping and root uprighting actions and for defining predetermined tip values. The bracket includes pivot edges for permitting pivotal movement between the bracket and the archwire, and a stop for limiting over-root-uprighting. It may also have a stop for limiting over-crown-tipping.

2 Claims, 4 Drawing Sheets

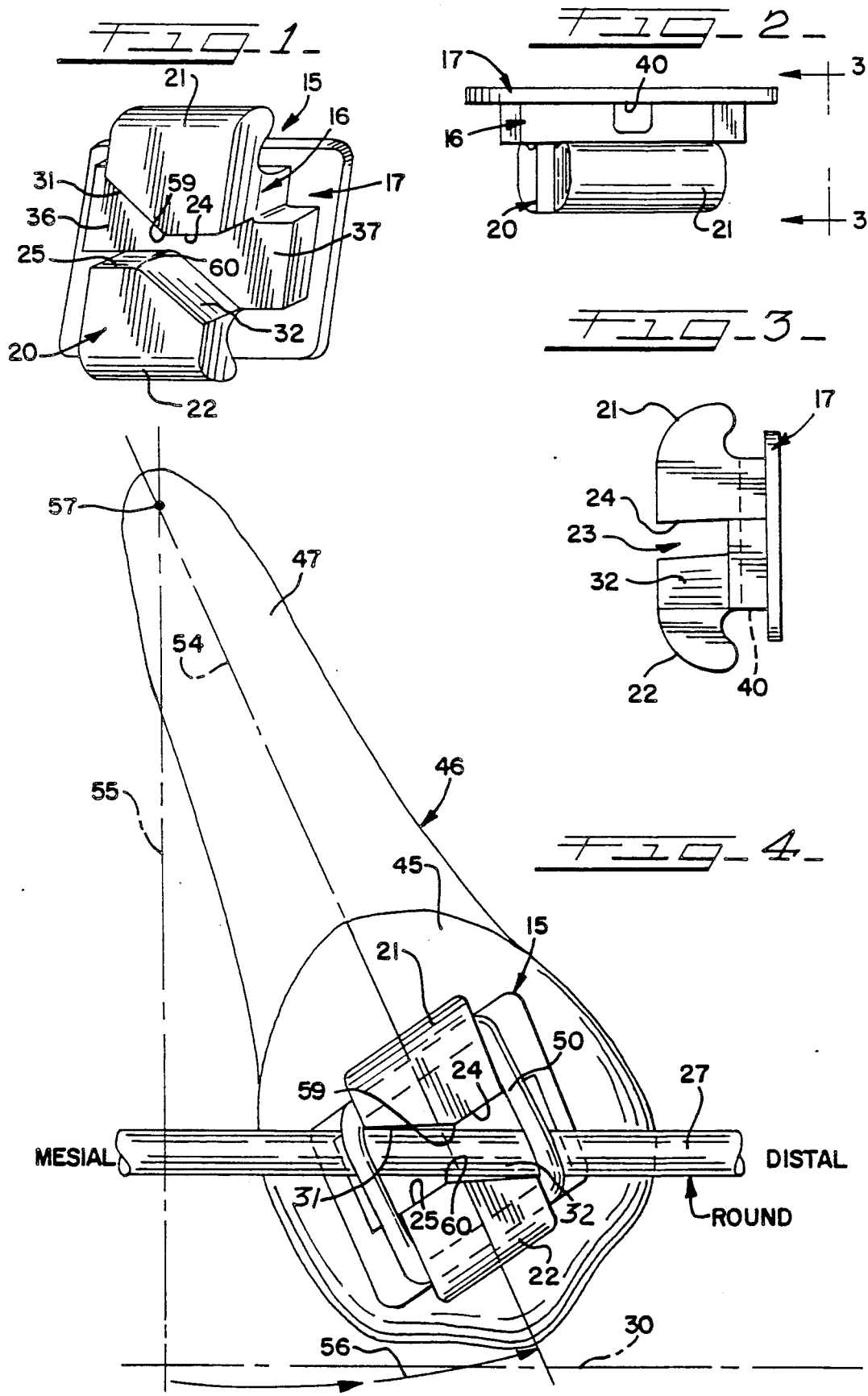

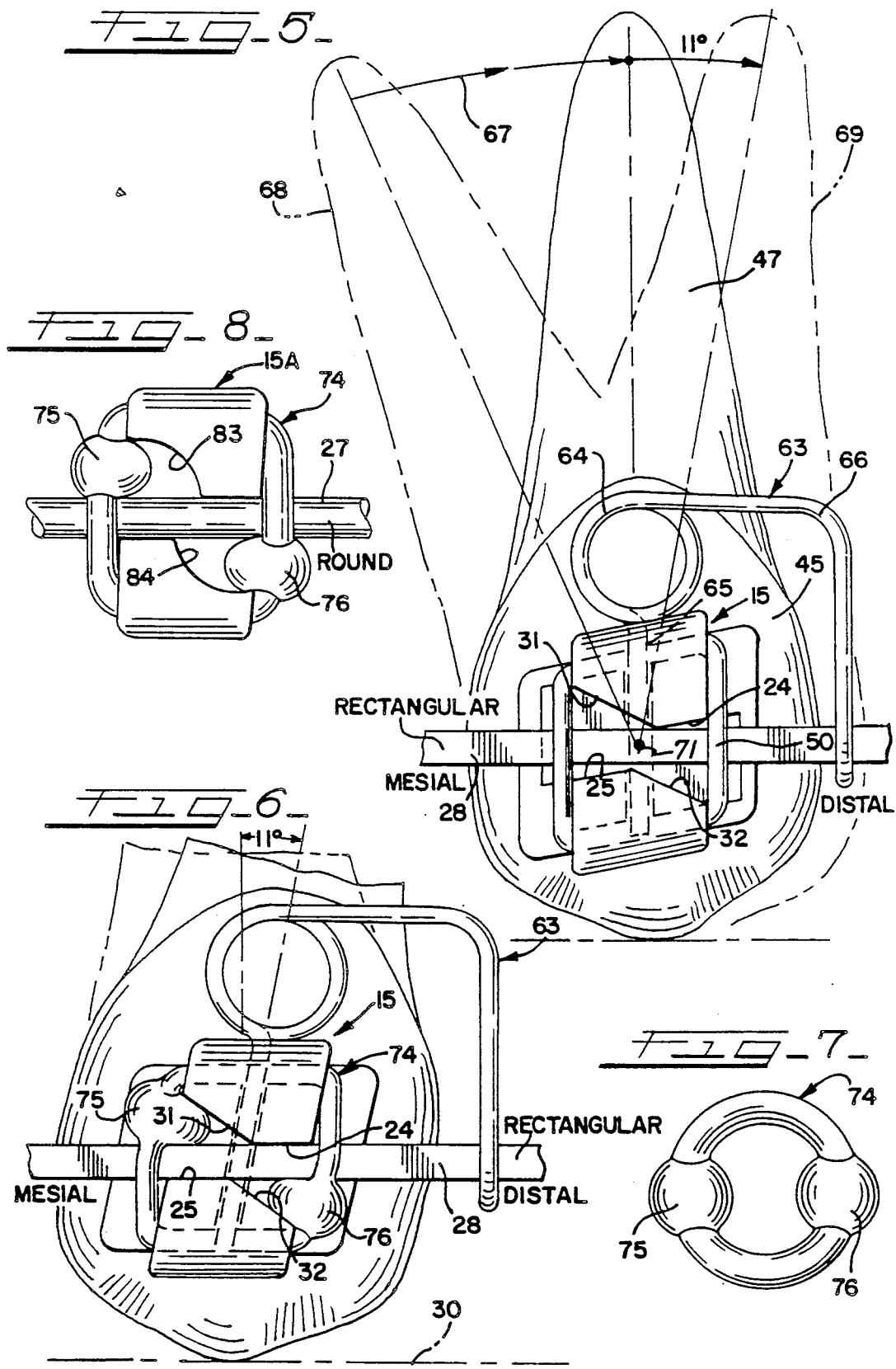

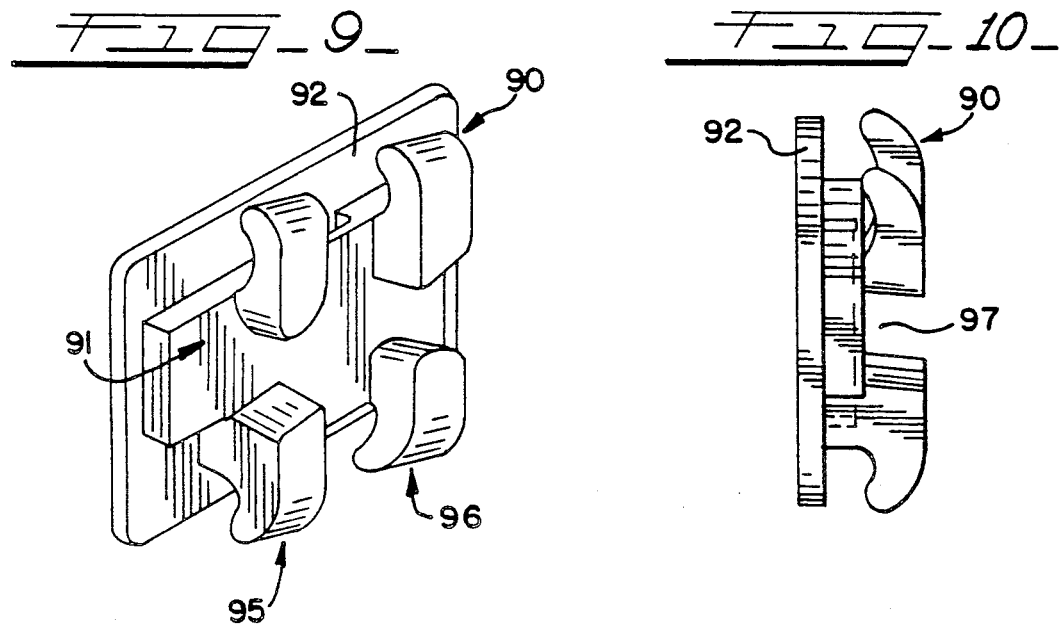
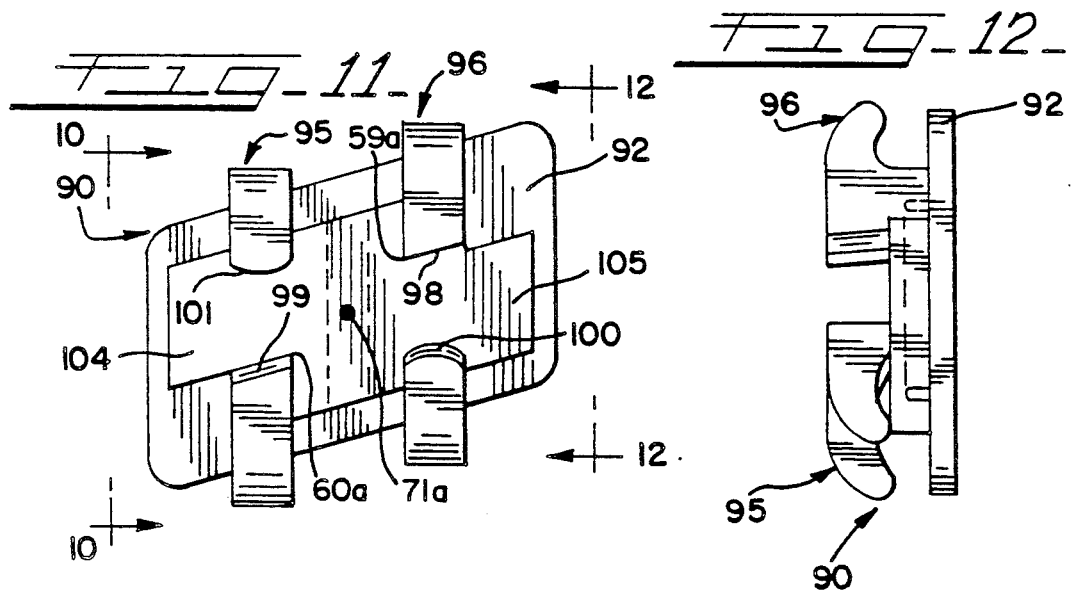
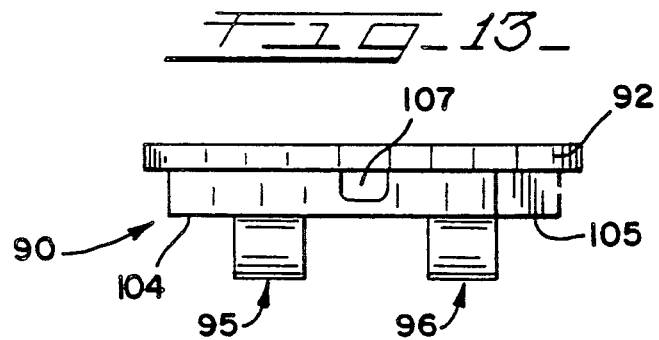

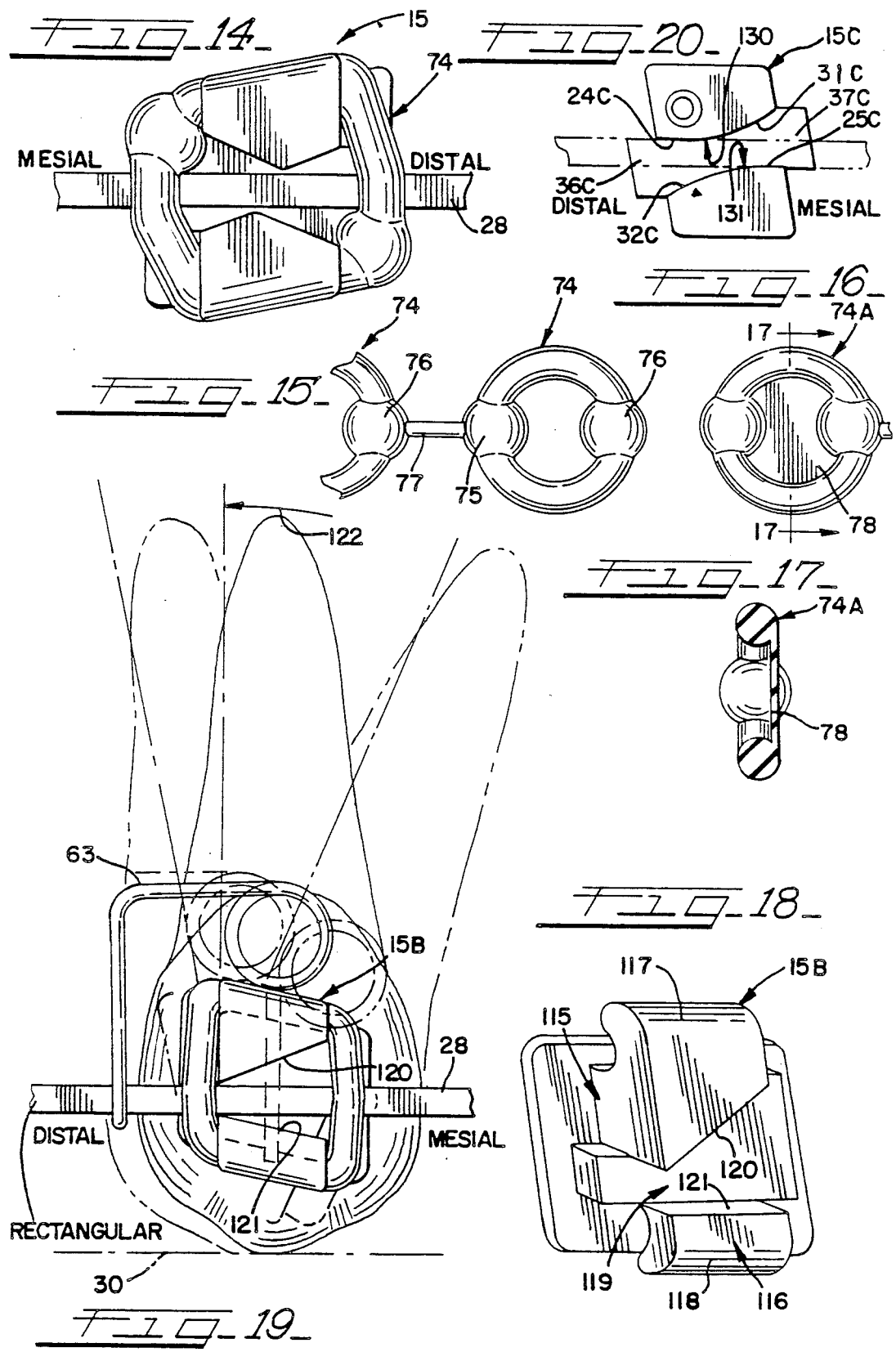

BRACKET FOR PERMITTING TIPPING AND LIMITING UPRIGHTING

This application is a continuation of application Ser. No. 07/054,837, filed Jun. 4, 1987, now U.S. Pat. No. 4,877,398, issued Oct. 31, 1989, which is a continuation-in-part of application Ser. No. 07/039,530, abandoned Apr. 16, 1987, which is a continuation-in-part of application Ser. No. 06/897,072, abandoned Jun. 26, 1986.

This invention relates in general to an orthodontic bracket for producing tooth movement, and more particularly to an orthodontic bracket for producing mesial-distal tooth movement through crown tipping and root uprighting movements, and still more particularly to an edgewise bracket for moving teeth with intraoral generated forces, while permitting a range of free crown tipping and producing predetermined final degree values of root uprighting and/or torque.

The terms "tipping" and "uprighting" relate to movements of teeth caused by the application of selected forces. Generally, "tipping" refers to either labial-lingual or mesial-distal movement of the crown of a tooth, while "uprighting" refers to either mesial or distal movement of the tip (apex) of the root of a tooth. Tipping herein will be in the mesial-distal direction unless otherwise specified. Torque generally refers to the movement of the root of a tooth in the labial-lingual direction as a result of forces being applied to the crown of the tooth. Thus, crown movement will be referred to as tipping, while root movement will be referred to as uprighting or torqueing. The use of "and/or" herein is intended to cover three alternatives. For example, "mesial and/or distal archwire stops" means mesial and distal archwire stops or mesial archwire stops or distal archwire stops.

BACKGROUND OF THE INVENTION

There are a number of orthodontic techniques in use, the most common being the edgewise and the Begg techniques. Within the ambit of the edgewise technique, the most popular form is referred to as the straight-wire technique, although all forms of edgewise technique generally use edgewise brackets having horizontally extending archwire slots, the openings of which face horizontally. The bracket configuration for the Begg technique utilizes a vertically extending archwire slot which permits materially greater free tipping of teeth during treatment than heretofore known edgewise brackets. Free tipping action with edgewise brackets is very limited and only possible when a wire smaller than the archwire slot is employed, so that there is a sloppy or loose fit between the archwire and the slot.

The need for moving teeth mesial-distally is usually caused by spaces created by small or missing teeth. It is customary in the Begg technique to close these spaces or move teeth by first tipping the clinical crowns toward the open area and then uprighting the root so that the final uprighting or tip angle of the tooth is at a predetermined inclination. For closing such open sites when using the edgewise technique, it is customary to bodily move the teeth. It is well known that the forces needed, discomfort, and time required for closing spaces by tipping and uprighting movements is much less than that required for bodily moving the teeth.

Where teeth are initially tipped and standard edgewise brackets are mounted on the teeth to provide treatment through the edgewise technique, it is difficult, if not impossible, to engage a relatively large diameter or stiff archwire into the respective archwire slots. The same problem exists if teeth with edgewise brackets become tipped during the course of treatment. And yet, such larger diameter, stiffer archwires are often necessary to control the vertical and horizontal positions of the teeth in the jaws. Therefore, weaker and more flexible archwires must be utilized which can cause the anterior teeth to elongate. The most common method of preventing elongation includes application of heavy extraoral forces to the upper archwire.

If resilient archwires are deflected to fully engage edgewise slots where teeth are tipped, the occlusal plane or level of the biting edges of the teeth can be adversely affected by the forces applied through these archwires. Usually, the anterior teeth are elevated out of their sockets, resulting in an unhealthy deep anterior overbite condition. This is one of the reasons tipping of teeth in the edgewise technique is avoided. Moreover, the very design of the well known edgewise bracket prevents teeth from becoming tipped during treatment. It will be understood that the "occlusal plane" as used herein is a plane generally containing the contact points between the upper and lower teeth, and it generally lies ninety degrees to the vertical lines used for references when determining and describing the amount of tip desired for each tooth.

In Begg brackets, sometimes referred to as ribbon arch or light-wire brackets, it is usually possible to engage larger stiffer archwires in the archwire slots because the opening of the slots face vertically, thereby permitting ease of archwire engagement in brackets mounted on tipped teeth.

It has been suggested that the edgewise slot be shortened mesiodistally or altered to define opposing one point contacts to increase the degree of tipping. However, the former still restricts tipping, and the latter (altered) bracket can permit free tipping but has no ability to control or create the final, desired degree of uprighting.

While Begg brackets that permit but limit tipping and/or uprighting are known, edgewise brackets with similar functions are not known.

It has also been known to use combination brackets having both labially or horizontally facing horizontal archwire slots and gingivally facing vertical archwire slots where the vertical slots would be used during early stages of orthodontic treatment to allow the crowns of the teeth to tip toward their final positions. Then in the final stage an archwire can be deflectively received by the horizontal slots. However, while this will tend to upright the teeth, it will also tend to deepen the anterior bite condition and therefore headgear for producing extraoral forces may be required to counteract such adverse conditions. Headgear comprises using the patient's head or neck as a point of anchorage for delivering relatively heavy forces to the teeth.

Where combination brackets are used, it has also been suggested that two archwires be used, one in the horizontal slots and one in the vertical slots. A lighter more resilient archwire is deflected to seat in the angulated horizontal slots, while a heavier stiffer archwire is engaged without deflection into the vertical slots. The heavy wire helps stabilize the reciprocal forces delivered to the teeth from the lighter deflected archwire as it returns to its passive straight arch form. The use of two archwires is cumbersome and creates undesirable food traps.

In the edgewise procedure teeth are moved bodily in their upright positions toward one another to close spaces. Such movement requires two to three times as much force and time as when moving teeth in the Begg technique by a combination of tipping and uprighting forces. Normally, the crown tipping is followed by root uprighting. Moreover, the bodily movement method in the edgewise technique most often requires the application of extraoral force supplied by headgear. Clinical experience indicates that the use of such extraoral force has caused hundreds of soft tissue injuries including many cases of partial and even total blindness as a result of accidents occurring while wearing headgear.

SUMMARY OF THE INVENTION

The present invention obviates the above-mentioned difficulties in providing an improved edgewise bracket for moving teeth to retract teeth and/or close spaces which essentially eliminates the need to apply extraoral force through headgear.

The present invention relates to an improved edgewise bracket. While particularly useful for moving teeth and closing spaces in a straight-wire technique, it can be used with any type of technique. The bracket of the invention resembles an edgewise bracket in that it has one or more tie wings and a horizontal labially opening archwire slot. The archwire slot is sized and formed to receive either a heavy or a light archwire and a heavy archwire can be seated in the slot even when the tooth is tipped mesiodistally. Crown tipping and root uprighting movements may be accomplished by use of suitable elastics, springs and other auxiliaries intraorally.

For the purpose of accommodating the use of uprighting springs and other auxiliaries, a vertical slot can be provided in the base of the bracket at the tooth-mounting side. The bracket of the invention may be provided with single or twin tie wings. While an archwire slot in a twin tie wing bracket is not continuous, it is considered to be the archwire slot for the bracket. With respect to either bracket, rotation control extensions extending mesially and distally from the archwire slot may also be provided.

It is therefore an object of the present invention to provide a new and improved edgewise bracket for moving teeth through tipping and uprighting functions.

Another object of the present invention is in providing a new and improved edgewise bracket for use in edgewise and other techniques having uprighting limit surfaces that avoid overmovements.

A further object of the present invention is in the provision of a new and improved edgewise bracket for use in moving teeth which substantially eliminates the need to apply extraoral forces.

A further object of the present invention is in the provision of a new and improved edgewise bracket for use in repositioning teeth anterior-posteriorly which substantially eliminates the need to use headgear.

Another feature of the invention is to provide an elastic ligature having enlargements for disposition between the archwire and bracket engaging surfaces for the purpose of either maintaining a predetermined relation between the archwire and the bracket or providing additional forces to move the bracket relative to the archwire until the control surfaces seat on the archwire. The elastic ligature may be provided in chain form where filaments or links interconnected adjacent ligatures and where adjacent ligatures may be mounted on adjacent brackets so that the filaments or links additionally function to apply a closing force between the brackets. Another form of elastic ligature includes having a sheet or panel of material of the same type as the ligature along one face so that when the ligature is applied to a bracket the sheet or panel covers the outer face of the bracket to enhance the comfort of the patient against any of the edges of the bracket and also for the purpose of improving the aesthetics.

Another object of the present invention is in providing a new and improved edgewise bracket for moving teeth and to be used in conjunction therewith an elastic ligature having enlargements functioning to either apply additional force between the archwire and bracket to encourage crown tipping or root uprighting or to maintain a given position of orientation between the archwire and bracket.

Still another object of the present invention is in the provision of a new and improved edgewise bracket for moving teeth having rotation control extensions or wings at the mesial and/or distal sides of the bracket along the archwire slot and which also may be of the single or twin tie wing form.

A further object of the invention is to provide an improved elastic ligature having a web portion that will serve to improve the aesthetics of fixed appliances and to protect the mouth against any sharp edges on the bracket face.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 1 is a perspective view of one form of the bracket of the present invention;

FIG. 2 is a top plan view of the bracket of FIG. 1;

FIG. 3 is an end elevational view of the bracket of FIG. 1 taken along line 3—3 of FIG. 2;

FIG. 4 is a front elevational view of an upper left cuspid tooth having a bracket of the invention mounted thereon and having an archwire secured in the archwire slot and illustrating the distal tipping position of the crown;

FIG. 5 is a front elevational view of an upper left cuspid tooth with the bracket of the invention mounted thereon like that illustrated in FIG. 4 and also illustrating the use of a root uprighting spring and the sequential movement of the tooth from a starting position to the desired inclined position and further illustrating the tooth in solid lines in the final desired position;

FIG. 6 is a fragmentary view of a tooth having the bracket of the invention mounted thereon and illustrating the use of an uprighting spring together with the unique elastic ligature of the invention having force module enlargements;

FIG. 7 is a plan view of the elastic ligature shown in use in FIG. 6 in a relaxed state and which is termed a "satellite ring";

FIG. 8 is a front elevational view of a modified bracket of the invention illustrating another form of control engaging surfaces and also the use of the unique elastic ligature shown in FIG. 7;

FIG. 9 is a perspective view of a modified bracket of the invention with twin tie wings;

FIG. 10 is an end elevational view of the bracket of FIG. 9 taken along line 10—10 of FIG. 11;

FIG. 11 is a front elevational view of the bracket of FIG. 9;

FIG. 12 is an end elevational view of the bracket of FIG. 9 and of the opposite end of the bracket of FIG. 10 taken along line 12—12 of FIG. 11;

FIG. 13 is a top plan view of the bracket of FIG. 9;

FIG. 14 is a front view of a bracket according to the invention and a ligature ring mounted in place retaining the archwire in the bracket archwire slot wherein the ligature includes enlargements for producing a movement force between the archwire and the bracket and also illustrating the bracket in a position prior to disposition in the final upright position;

FIG. 15 is a modification of the elastic ligature shown in FIG. 7 in that a link or filament is provided between two adjacent ligatures for purposes of connecting them together and also then applying a force between two or more adjacent teeth;

FIG. 16 is a further modification of the ligature and including a thin web along one face to serve when the ligature is mounted on a bracket for purposes of improving the aesthetics of the bracket and also to assist in protecting the tissue against any sharp edges on the bracket;

FIG. 17 is a vertical sectional view of the ligature of FIG. 16 and taken substantially along line 17—17 thereof;

FIG. 18 is a perspective view of a modified bracket according to the invention having a wedge-shaped archwire slot;

FIG. 19 is a front elevational view similar to FIG. 5 but illustrating the bracket of FIG. 18 mounted on an upper right cuspid and in combination with an archwire connected by an elastic and an uprighting spring; and FIG. 20 is a front elevational view of a modification which differs from the bracket of FIG. 1 in that the faces of the archwire slot are curvilinear, and it is designed for an upper right cuspid.

DESCRIPTION OF THE INVENTION

The improved bracket of the invention may be generally referred to as an edgewise bracket since it includes a horizontally opening archwire slot in its outer face and may have one or more ligature tie wings. The archwire slot may even have torquing surfaces for applying a predetermined torque to a tooth. While the bracket of the invention may be used in any one of many edgewise techniques, it may also be used in other techniques. Normally, it will be used in a system having edgewise-type brackets.

The bracket of the invention moves teeth mesial-distally by a combination of tipping and uprighting actions. Either round or rectangular archwire may be used during this tooth-moving process. Where torque action is also desired, rectangular cross-section archwire can be used for engagement with torquing surfaces.

Teeth that require orthodontic treatment are quite often tipped mesial-distally at the beginning of or during the course of movement. The unique configuration of the horizontal archwire slots of this invention permits the initial engagement of an archwire in the brackets on such tipped teeth with little or no deflection. This same archwire slot design permits the teeth to tip mesial-distally during treatment without deflecting the archwire which could require greater force to be applied and/or result in loss of control in the vertical dimension, i.e., the undesired depression and/or elongation of teeth.

Inasmuch as both elastic traction devices and/or springs may be used during the tooth-moving process, and either or both of which may apply forces of a magnitude that could overpower a highly resilient archwire such as of the nickel titanium or metal core-plastic type, it is advantageous to use a relatively stiff or rigid archwire. With the bracket of the present invention, it will be appreciated that the archwire can be disposed in substantially parallel relation to the occlusal plane even when engaged in mesial-distally tipped teeth. Thus, the archwire can be of a size and stiffness compatible with the reciprocal movement forces to be encountered so that the tipping and uprighting movements produced will give the desired results.

The bracket of the invention can be made of a suitable metal, such as stainless steel, and it may be machined, sintered or cast in any known manner. The bracket may be made and then suitably secured to a base that would be bondable to a tooth, or the bracket and base may be cast together as a single unit. While it is preferred that the bracket be made of metal, it will be appreciated that it could be made of ceramic or plastic or plastic with a metal lined archwire slot. It is important that the bracket have sufficient strength to withstand the forces employed during the tooth-moving process. It may also be appreciated that the bracket may otherwise be attached to a tooth by the usual banding methods. In all cases the bracket will be mounted to the crown of the tooth and aligned with the long axis of the crown so that the tooth will attain the position finally desired.

The edges of the brackets, while illustrated as being generally sharp, would be rounded or smoothed in actual practice to be comfortable in the mouth. Where the bracket may be cast, the edges and sides may even be rounded or curved. As an example, the mesial and distal sides or the occlusal and gingival edges may be curved when cast and still retain a generally parallel appearance.

For purposes of describing the invention and for purposes of clarity, the drawing illustrations principally relate to showing the straight-wire technique wherein the archwire will be generally passive and disposed in substantially parallel relation to the occlusal plane, and the archwire slot in each bracket may be different to achieve varying degrees of final root uprighting according to the desires of the orthodontist and the needs of each patient.

Referring now to the drawings, and particularly to the embodiment of FIGS. 1 to 6, the single tie wing version of the invention is designated generally by the numeral 15 and includes a bracket body 16 on a base 17 of the well known type that is bondable to the crown of a tooth, as illustrated in FIGS. 4, 5 and 6. It will be positioned on the crown preferably centered in the middle third area of the crown between the incisal edge and the gingiva.

The bracket body 16 includes a tie wing 20 having an upper or gingival tip 21 and a lower or occlusal tip 22. Centrally disposed of the tie wing is a rectangular in cross section archwire slot 23 opening horizontally and having diagonally opposed uprighting stops 24 and 25. Thus, the tie wing 20 includes means in the archwire slot 23 for receiving an archwire such as the round archwire 27 shown in FIG. 4 or the rectangular archwire 28 shown in FIGS. 5 and 6. The archwires illustrated are of a size that essentially fills the archwire slot when the tooth is in the final upright position. As mentioned, the archwires are disposed generally parallel to the occlusal plane 30 as in the straight-wire technique.

The body 16 of the bracket version in FIG. 1 also includes upper and lower tipping stops 31 and 32 that may function to limit crown tipping movement during the tooth movement process to prevent overtipping. The surfaces of these stops are illustrated as being flat but also may be of any other configuration and still perform the limited tipping function. Where the surfaces are flat, they do not normally have any torque built into them relative to the bracket, although such could be provided if desired. The surfaces as shown are parallel to each other as are the uprighting surfaces. Moreover, the tipping stops are diagonally opposed on the tie wing as viewed in elevation, such as seen particularly in FIGS. 4, 5 and 6.

Thus, an uprighting stop surface will be generally in a directly opposed relation to a tipping stop surface, and the mesial or distal edges of both will define the mesial and distal openings of the archwire slot. For purposes of providing additional rotational control, rotation wings or extensions 36 and 37 are shown at opposite sides of the tie wing and extend from the openings defined by the outer ends of the stops. These extensions extend the base of the archwire slot beyond the edges of the bracket tie wing and against which the lingual side of the archwire would bear and engage during the coaction between the archwire and the bracket. They would function no matter what disposition exists between the archwire and the bracket, as illustrated in FIGS. 4, 5 and 6. It will also be appreciated that the bracket of the invention may be provided without these extensions as they do not affect the function of tipping and uprighting. They only function to provide better rotational control.

A vertical slot 40 is provided in the bracket body at the base 17 for the purpose of facilitating the anchoring of an auxiliary such as an uprighting spring, as illustrated in FIGS. 5 and 6. It will be appreciated, however, that the bracket of the invention is not dependent upon having such a vertical slot, as there are other possible methods of anchoring an uprighting spring to the bracket. The vertical slot 40 is parallel to and coincident with the vertical central axis of the bracket as especially shown in FIGS. 5 and 6. It will also be noted that the vertical slot 40 is disposed behind the tips of the tie wing 20.

The bracket 15 of the invention is shown mounted to the crown 45 of a tooth 46 in FIGS. 4, 5 and 6 so as to illustrate the tipping and uprighting functions in the tooth-moving process. The desired objective is to orient the crown and position it in the ideal location, which normally involves some degree of crown tipping or root uprighting, or a combination of both. When closing a space the crown is first tipped toward the open site and when disposed in that site the root is uprighted to a position where the long axis of the crown reaches a desired tip angulation. Further, the angles of the crown tipping stops relative to the vertical axis of the bracket can depend upon the amount of retraction or protraction desired for a tooth.

The angles of inclination or locations of the archwire stops will depend upon the specific tooth for which the bracket is designed as well as the movement function desired by the orthodontist. For example, when the bracket is mounted on a tooth that is intended to undergo considerable retraction in the mouth, the distal crown tipping stop would normally have a greater angle of inclination than when minimum retraction is desired. For a specific tooth the angle of inclination for the root uprighting stop would tend to be the same for all patients depending on the orthodontist's treatment goals, while the angle of the crown tipping stop would depend upon the amount of retraction or protraction desired for the tooth, depending on the patient's original malocclusion. More particularly, a bracket of the type illustrated where tipping movement can be accomplished between the bracket and the archwire, the crown will first be tipped mesially or distally, then held to prevent return to its original location, while the root is uprighted over the crown to the ideal or desired final inclination. These so-called ideal final inclinations may differ among orthodontists, as does beauty in the eyes of the beholder. Where the term "angle of inclination" is used herein, it is intended to cover positioning of a tooth vertically or at an inclined position to vertical. However, commonly used ideal or desired angles of inclination for each particular tooth have been proposed. The angle of inclination is measured to the distal between the vertical axis of the mouth and the long axis of the clinical crown of a tooth. For example, the common ideal angles of inclination for the upper teeth, left and right, are:

5 degrees for a central,
9 degrees for a lateral,
11 degrees for a cuspid,
2 degrees for a bicuspid, and
5 degrees for a molar.

The common inclination angles for lower teeth, left and right, are:

2 degrees for centrals and laterals,
5 degrees for the cuspids, and
2 degrees for the bicuspids and molars.

The tooth 46 illustrated in FIGS. 4, 5 and 6 is an upper left cuspid, and therefore the angle of inclination for the uprighting stops is 11 degrees. Depending upon whether the bracket is designed to accomplish average, maximum or minimum retraction or protraction, the angle of the crown tipping stops may vary. However, a maximum crown tipping angle may be utilized on all teeth where the orthodontist would monitor the tipping and remove the crown tipping forces when the desired tipping is accomplished for each tooth. At some point after this, the uprighting of each tooth would commence with the application of a suitable uprighting force or forces by use of suitable intraoral force generating devices.

The archwire 27 is retained in the archwire slot of the bracket by a suitable ligature such as the elastic ligature 50 of the well known type as shown in FIG. 4 that would be stretched and hooked over the upper and lower tie wing tips 21 and 22 after the archwire is disposed in the archwire slot. It may also be appreciated that a suitable wire ligature may be provided, although an elastic ligature is preferred in view of its relative ease of placement and flexibility which more easily permits relative movement between the bracket and the archwire. Moreover, a unique elastic ligature may be used with the bracket of the present invention to produce tipping or uprighting forces, as shown in FIG. 7 and hereafter explained.

For purposes herein, the long axis of the tooth 46 represented by the broken line 54 in FIG. 4 coincides with the long axis of the crown 45, it being appreciated that the long axis of the tooth extends through the crown 45 and the root 47. Not all cuspid teeth or other teeth would have a root as straight as that illustrated. Concern here is for providing the desired inclination of the crown, and therefore the crown axis will most often be referred to when relating to tooth disposition.

As seen in FIG. 4, the vertical axis of the patient's mouth is indicated by the broken line 55 which normally is at ninety degrees to the occlusal plane that is usually parallel to the archwire 27. At the beginning of treatment, the long axis of the tooth illustrated by the broken line 54 may have been substantially vertical. The disposition of the tooth in FIG. 4 is that caused by a tipping force to obtain distal crown tipping. Ideally, such movement would be on the order of a swinging movement in the direction of arrows 56 substantially about the pivot point 57 near the root apex such as from the vertical axis 55 to the position shown by the long axis 54 of the crown. In this position, it can be appreciated that the archwire 27 will touch the crown tipping stops 31 and 32, which stops will then prevent further tipping even though the tipping force is not fully expended. Thus, the tipping stops automatically limit the tipping movement, and it may be appreciated that the angle of these stops relative to the vertical axis of the bracket may be whatever is desired, that is, the angle could be greater or less than that of the tipping stops 31 and 32 of the bracket illustrated. It is also possible that depending upon the timing between orthodontic visits that the tipping force may be fully expended and the archwire may not fully engage the tipping stops but that the orthodontist might remove the tipping force and commence application of an uprighting force. In any event, as already mentioned, overtipping can be prevented by the tipping stops. It must be realized that the pivot point 57 or center of rotation of tipping may occur anywhere between the root apex and the bracket slot.

The relative movement between the bracket and the wire will be about pivot edges or areas 59 and 60 which are respectively defined between the surfaces of tipping and uprighting stops 31 and 24 respectively and between the tipping and uprighting stops 32 and 25 respectively, so that the pivot edges will function as a fulcrum about which the bracket will pivot on the archwire 27. The pivot edges are at the ends of the tipping and uprighting stops. While these edges are illustrated to be generally sharp, they may be rounded or the entire length of the archwire faces may be rounded as in the embodiment of FIG. 20. The archwire will generally be considered the reference line along and about which tipping and uprighting occurs. The bracket and pivot edges may also move mesially or distally along the archwire as the crown is tipped or the root uprighted. Preferably, these pivot edges will be laterally offset from one another, as illustrated in FIGS. 4, 5 and 6, although it will be appreciated that they could also be vertically coincident and still permit a degree of tipping and limited uprighting where the pivot edges are at one side, as seen in FIG. 18.

Once the desired tipping movement has been accomplished, it is then the objective to complete movement of the tooth to upright the root 47. One method of applying an uprighting force is by using an uprighting spring such as the spring 63 shown in FIGS. 5 and 6. This spring includes a power coil 64 and extending therefrom a tail 65 that would be received in the vertical slot 40 of the bracket and a power arm 66 that would be hooked over the archwire. The uprighting spring would function in the usual manner whereby, mounted as shown in FIGS. 5 and 6, it would cause the root of the tooth to upright in the direction of the arrow 67 from the broken line position 68 through the substantially vertical position to the broken line position 69. The final position 69 would approximate the inclination angle desired of the particular tooth being moved, and as previously stated for an upper cuspid tooth this could be about 11 degrees from the vertical axis. Root uprighting movement would generally be in the form of a pivotal movement of the tooth substantially about the pivotal or generally horizontal axis 71 shown in FIG. 5 which would preferably be at the center of the bracket 15. When the uprighting stops 24 and 25 would abut the archwire 28, as in FIG. 6, uprighting movement would cease automatically and the tooth would be in the desired inclined position. Thus, even if the period of time between orthodontic visits was such that further uprighting could take place, it would not, as the bracket would prevent further uprighting.

Where there might be needed additional uprighting force or where it may not be possible to use an uprighting spring, the unique elastic ligature or elastic appliance of the invention could be used to generate movement forces. This ligature is particularly shown in FIG. 6 in mounted relation on a bracket and generally designated by the numeral 74 and in FIG. 7 in its passive state where it is configured like a satellite ring. Thus, the ligature is in the form of a ring with one or more enlargements. It could be made of the same material as the elastic ligature 50 but would additionally include at predetermined locations enlargements or nodules 75 and 76 that would function to produce a force when disposed between the archwire and a portion of the bracket and compressed. While the ligature illustrated comprises a strand with two enlargements therealong in equally spaced apart relation, it should be appreciated that it could be provided with but a single enlargement. In the illustration shown in FIG. 6, that force would produce uprighting movement as the enlargements are disposed between the archwire 28 and the tipping stops 31 and 32.

The size of each enlargement could be such that it would be compressed when disposed between the archwire and the tipping stops to produce a wedge separating force between the stops and the archwire even when the archwire is in engagement with the other stops. The ligature would maintain the archwire in seated position on the stops even if the uprighting spring were to fail. In this respect, the unique elastic ligature would be a backup to the uprighting spring. When mounted on a bracket over the wire, it would be stretched and tight-fitting.

It will be appreciated that the ligature 74 could be mounted such that the force nodules 75 and 76 would be disposed between the archwire and the uprighting stops 24 and 25 if it were desired to provide additional tipping force during the tipping movement of the tooth.

While normally an uprighting spring will be used as a primary force to induce movement between the bracket and the archwire, there may be situations where only the satellite ring 74 is needed to induce the uprighting force, as illustrated in FIG. 14.

The enlargements on the satellite ring could be more rigid than the elastic ring itself so that a more positive application of force would be produced by the ring. This could be accomplished by making the enlargements harder or less elastic than the strand when the same type of material is used for both, or by making the enlargements of a different material altogether. While the enlargements are shown as ball shaped, they may be oval or otherwise shaped.

The elastic appliances or satellite rings 74 may also be provided in chain form and interconnected by elastic filaments or links 77, as shown in FIG. 15. While the link 77 is illustrated as being connected between enlargement portions of adjacent rings, it will be appreciated that the links may interconnect at other points along the rings. The connecting link 77 may be suitably sized to function as a force transmitting member between adjacent rings when they are mounted on adjacent brackets. In this respect the link 77 would serve to apply a closing force between brackets and teeth on which the brackets are mounted. In the event that the link is not needed, it may easily be cut to separate adjacent rings. Thus, the satellite rings may be packaged in chain form and thereafter used singly or in plural.

The satellite ring may also be modified by adding a thin sheet or panel 78 of elastic material, as seen in the modified satellite ring 74a shown in FIGS. 16 and 17. The sheet 78 would be integrally molded with the other portions of the ring and would cover along one entire face of the ring and be positioned outwardly when the ring is mounted on a bracket to add comfort by completely covering the outer face of the bracket and any sharp edges, and to also enhance the aesthetics of the bracket. The elastic material of the ring may be clear or of any suitable color such as a tooth or cheek color or even a bright color. As seen particularly in FIG. 17, the sheet of material 78 is relatively thin compared to the total front-to-back thickness of the ring and is positioned at one face so as to not interfere with the operation of hooking the ring over the tie wings of a bracket.

A modified bracket is illustrated in FIG. 8 and designated 15A which differs from the bracket 15 only in the configuration of the tipping stops that are shown to have a concave surface between the pivot edges and the outer edges of the bracket. These surfaces 83 and 84 define modified surfaces engaging the enlargements 75 and 76 of the endless ligature 74. The enlargements would fit in tighter against the bracket and would provide essentially the same type of root uprighting force as provided where the stops are straight from the pivot edges to the outer edges of the bracket, as in the bracket 15. This embodiment also illustrates that the bracket of the invention, relative to the shape of the part permitting tipping, has other forms.

The twin tie wing version of the present invention is shown in FIGS. 9 to 13. This bracket is generally designated by the numeral 90, and generally, except for having plural tie wings instead of a single tie wing, it is structured like and functions like the single tie wing bracket 15. This bracket includes a body 91 on a base 92 that is bondable to the crown of a tooth in the well known manner. The body further includes parallel tie wings 95 and 96 having an archwire slot 97 defined by diagonally disposed uprighting stops 98 and 99 and diagonally disposed tipping stops 100 and 101 which are respectively opposite uprighting stops 98 and 99, and fulcrum means in the form of pivot points 59a and 60a that permit rotation of the bracket substantially around a generally horizontal axis 71a in a like fashion to the operation of bracket 15, as illustrated in FIG. 5. Thus, each tie wing includes an uprighting stop and a tipping stop.

The uprighting stops 98 and 99 are defined by flat surfaces parallel to each other and which may have any desired torque value. The tipping stops are illustrated as having arcuate surfaces, as they function only to stop movement between the bracket and the archwire during crown tipping movement. Thus, the uprighting stops can function not only to control root uprighting movement but can also function to control torque. All four stops could have arcuate or even knife-edge faces and still function to control tipping and uprighting.

In order to provide additional rotational control, rotation extensions or wings 104 and 105 extend from the outer edges of the tie wings and in the area of the openings defined between the stops. These extensions function in the same manner as those of the single wing version already described.

A vertical slot 107 is provided in the body adjacent the base 92 for purposes of anchoring auxiliaries such as an uprighting spring in the same manner as described with respect to the single wing bracket version. This vertical slot is coincident with the central vertical axis of the bracket.

Except for the increased width of the twin wing bracket 90 over the single wing bracket 15 that will provide better rotational control, the function of the twin wing bracket would be the same as the single wing bracket during the movement of teeth generated from tipping and uprighting forces. Bracket 90 illustrates that the invention can be used in plural wing brackets as well as single wing brackets.

While the bracket 15 is the preferred embodiment for permitting tipping and uprighting movements along an archwire, and which includes an archwire slot having a general propeller like configuration, other configurations may be employed such as the bracket 15A in FIG. 8. Both brackets 15 and 15A include archwire slots within which the horizontal axis 71 of the bracket is centrally located as particularly illustrated in FIG. 5. Where it would be desired to shift the pivot point or where it would not make a difference as to the location of the pivot point, the archwire slot could take a wedge-shaped configuration as illustrated by the modified bracket 15B shown in FIGS. 18 and 19. This bracket includes a body 115 having a single tie wing 116, with upper and lower tie wing tips 117 and 118. A wedge-shaped archwire slot 119 is defined by an upper tipping stop or surface 120 and a lower uprighting stop or surface 121. As seen particularly in FIG. 19 where the bracket is mounted on a tooth and in combination with the archwire 28 and the uprighting spring 63, the pivot point of the bracket about which movement occurs is at the left or distal edge of the bracket where the bracket is mounted on an upper right cuspid and movement is produced in the direction of the arrow 122. Once the bracket is uprighted so that the uprighting surface 121 seats on the wire 28, uprighting action ceases. It will be appreciated that the uprighting stop 121 coacts with the archwire to stop the movement of the tooth at its desired tip angle relative to the occlusal. It will be further appreciated that a suitable torquing angle may be incorporated in the uprighting surface 121 to additionally provide torquing control. While a rectangular archwire 28 is shown mounted on the bracket 15B, it will be appreciated that for uprighting or tipping purposes the wire may be round. Further, it will be appreciated that during tipping action the tipping surface 120 will limit tipping action when and if it seats on the archwire 28. While the bracket 15B is illustrated as having a single tie wing, it will be appreciated that it may be structured with twin tie wings if so desired in a manner as heretofore appreciated. Further, it may be formed with more tie wing tips on the occlusal or gingival than on the opposite side, it only being necessary that at least one tie wing tip be at the gingival and at least one at the occlusal.

Another modified bracket according to the invention is shown in FIG. 20, which differs from the embodiment of FIG. 1 in that the entire archwire bearing faces between the mesial and distal edges of the bracket are curvilinear. This bracket is for an upper right cuspid.

With reference to FIG. 1, the pivot edges 59 and 60 appear rather sharp, although these edges could be somewhat rounded. These edges may even be more rounded than shown. Nevertheless, these pivot edges function to define a pivotal relation between the bracket and the archwire, as illustrated in FIGS. 5 and 6. Yet, it is not necessary that the edges 59 and 60 be sharp or approach a line configuration.

The bracket 15C includes opposed curvilinear archwire bearing surfaces 130 and 131. These surfaces are curvilinear between the mesial and distal sides of the bracket. Even though they are curvilinear, the areas of the faces adjacent the mesial and distal edges of the bracket function as stops for tipping and uprighting. Accordingly, the areas designated as 31c and 32c will function as tipping stops, while the areas designated 24c and 25c function as uprighting stops. As illustrated, the archwire is shown bearing against the uprighting stops, or more accurately the stops are shown bearing against the archwire which normally is maintained in the same attitude. Appreciating that movement of the bracket relative to the wire is very slow in the orthodontic process, the function of the bracket 15C will not differ from the function of bracket 15. As the bracket moves relative to the wire, the archwire faces will change their position in a rather smooth and orderly fashion.

The tip and torque for the bracket of the present invention, whether it be a single wing version or a double wing version, will be designed into the bracket according to the desired end result for any particular orthodontic treatment.

It will be understood that modifications and variations may be effected without departing from the scope of the novel concepts of the present invention, but it is understood that this application is to be limited only by the scope of the appended claims.

The invention is hereby claimed as follows:

1. An orthodontic bracket mountable on the crown of a tooth and coacting with a generally passive archwire extending substantially parallel to the occlusal plane, said bracket having a body with a horizontally opening archwire slot with means coacting with said archwire for permitting crown tipping including fulcrum means having opposed pivot means, and means coacting with said archwire for limiting root uprighting, said crown tipping means being at least at one side of the fulcrum means and defined by an open area for receiving the archwire during tipping, said means limiting root uprighting defining a plane with one of the pivot means which extends parallel to the occlusal plane when the tooth is uprighted, whereby said bracket is mesiodistally pivotal on the archwire about a generally horizontal axis, and said slot and archwire being sized so that the archwire substantially fills the area between the fulcrum means and the root uprighting limiting means when the tooth is uprighted.

2. An orthodontic bracket mountable on the crown of a tooth and coacting with a generally passive archwire extending substantially parallel to the occlusal plane, said bracket having a body with a horizontally opening archwire slot, the long axis of the bracket body being substantially aligned with the long axis of the crown as viewed from the buccal or labial, and said archwire slot having means for crown tipping, and means coacting with said archwire for limiting root uprighting to ultimately position the long axis of the crown at a desired mesiodistal inclination in the range of about 0 to 11 degrees to the vertical, said means for crown tipping including spaces on both sides of the archwire, said means for limiting root uprighting including stop means on both sides of the archwire for contacting the archwire when the bracket/tooth is in the final desired mesiodistal inclination and each said stop means defining a plane with corresponding stop means of at least two adjacent brackets which extends parallel to the occlusal plane when all teeth with said brackets are uprighted, said stop means being diagonally opposed, whereby said bracket is mesiodistally pivotal about a generally horizontal axis, and said archwire slot and archwire being sized so that the archwire substantially fills the vertical distance between the stop means when the long axis of the crown is uprighted to its ultimate inclination.

* * * * *

UNITED STATES PATENT AND TRADEMARK OFFICE
CERTIFICATE OF CORRECTION

PATENT NO. : 5,125,832
DATED : June 30, 1992
INVENTOR(S) : Peter C. Kesling

It is certified that error appears in the above-identified patent and that said Letters Patent is hereby corrected as shown below:

ON THE TITLE PAGE under [*] Notice, change date from "Oct. 3, 2006" to --October 31, 2006--;
      under Related U.S. Application Data, change "Ser. No. 897,072" to --Ser. No. 879,072--;

Col. 1, line 8, change "abandoned" to --filed--;
      line 9, after "1987," insert --abandoned,--;
      line 10, change "06/897,072, abandoned" to --06/879,072, filed--;
          after "1986" insert --,abandoned--.

Signed and Sealed this

Tenth Day of August, 1993

Attest:

MICHAEL K. KIRK

*Attesting Officer*      *Acting Commissioner of Patents and Trademarks*